US011193035B2

United States Patent
Kang

(10) Patent No.: US 11,193,035 B2
(45) Date of Patent: Dec. 7, 2021

(54) ULTRA LOW THERMO FUSION PVC PLASTISOL COATING AND TEXTILE PRINTING INK

(71) Applicant: Hack S. Kang, Pomona, NY (US)

(72) Inventor: Hack S. Kang, Pomona, NY (US)

(*) Notice: Subject to any disclaimer, the term of this patent is extended or adjusted under 35 U.S.C. 154(b) by 33 days.

(21) Appl. No.: 16/305,960

(22) PCT Filed: Jun. 1, 2017

(86) PCT No.: PCT/US2017/035457
§ 371 (c)(1),
(2) Date: Nov. 30, 2018

(87) PCT Pub. No.: WO2017/210431
PCT Pub. Date: Dec. 7, 2017

(65) Prior Publication Data
US 2019/0136083 A1 May 9, 2019

Related U.S. Application Data

(60) Provisional application No. 62/344,136, filed on Jun. 1, 2016.

(51) Int. Cl.
| | |
|---|---|
| C09D 7/61 | (2018.01) |
| C09D 7/63 | (2018.01) |
| C09D 7/65 | (2018.01) |
| C09D 5/00 | (2006.01) |
| C09D 11/03 | (2014.01) |
| C09D 11/106 | (2014.01) |
| C09D 127/06 | (2006.01) |
| A61L 2/08 | (2006.01) |
| C08K 5/10 | (2006.01) |
| C08K 5/00 | (2006.01) |

(52) U.S. Cl.
CPC ............ *C09D 127/06* (2013.01); *A61L 2/08* (2013.01); *C08K 5/10* (2013.01); *C09D 5/00* (2013.01); *C09D 7/61* (2018.01); *C09D 7/63* (2018.01); *C09D 7/65* (2018.01); *C09D 11/03* (2013.01); *C09D 11/106* (2013.01); *C08K 5/0016* (2013.01)

(58) Field of Classification Search
CPC .......... C09D 127/06; C09D 7/65; C09D 7/61; C09D 7/63; C09D 5/00; C09D 11/03; C09D 11/106; A01L 2/08; C08K 5/10; C08K 5/0016; A61L 2/08; A61L 12/08
USPC ................................................ 427/385.5, 385
See application file for complete search history.

(56) References Cited

U.S. PATENT DOCUMENTS

| | | | | |
|---|---|---|---|---|
| 3,466,223 | A * | 9/1969 | Beeler | C08K 5/103 428/213 |
| 4,115,292 | A * | 9/1978 | Richardson | C11D 3/38672 435/182 |
| 4,210,567 | A | 7/1980 | Kosters | |
| 4,904,825 | A * | 2/1990 | Govindan | C07C 215/40 562/84 |
| 5,292,565 | A | 3/1994 | Napier et al. | |
| 5,520,961 | A | 5/1996 | Lysell et al. | |
| 5,658,969 | A * | 8/1997 | Gerace | C08J 9/32 523/204 |
| 2007/0037926 | A1 * | 2/2007 | Olsen | C08L 27/06 524/569 |
| 2010/0113664 | A1 * | 5/2010 | Bradshaw | C08K 5/11 524/298 |
| 2012/0071598 | A1 | 3/2012 | Gosse et al. | |
| 2013/0137789 | A1 | 5/2013 | Olsen et al. | |
| 2014/0275376 | A1 | 9/2014 | Arendt et al. | |
| 2016/0075891 | A1 | 3/2016 | Funderburg et al. | |
| 2019/0315980 | A1 | 10/2019 | Kang | |

FOREIGN PATENT DOCUMENTS

CN 101812206 A * 8/2010

OTHER PUBLICATIONS

Tai, H.J., "Processing and Properties of High-Temperature Creep-Resistant PVC Plastisols," Polym. Eng. Sci., 39(7), Jul. 1999, pp. 1320-1327. (Year: 1999).*
CN 101812206 A, machine translation, IP.com. (Year: 2010).*

* cited by examiner

*Primary Examiner* — Josephine L Chang
(74) *Attorney, Agent, or Firm* — Fox Rothschild LLP

(57) ABSTRACT

The present invention relates to a novel plastisol composition that cures at a temperature much lower than conventional plastisols. Also disclosed is a method of applying the composition.

27 Claims, 1 Drawing Sheet

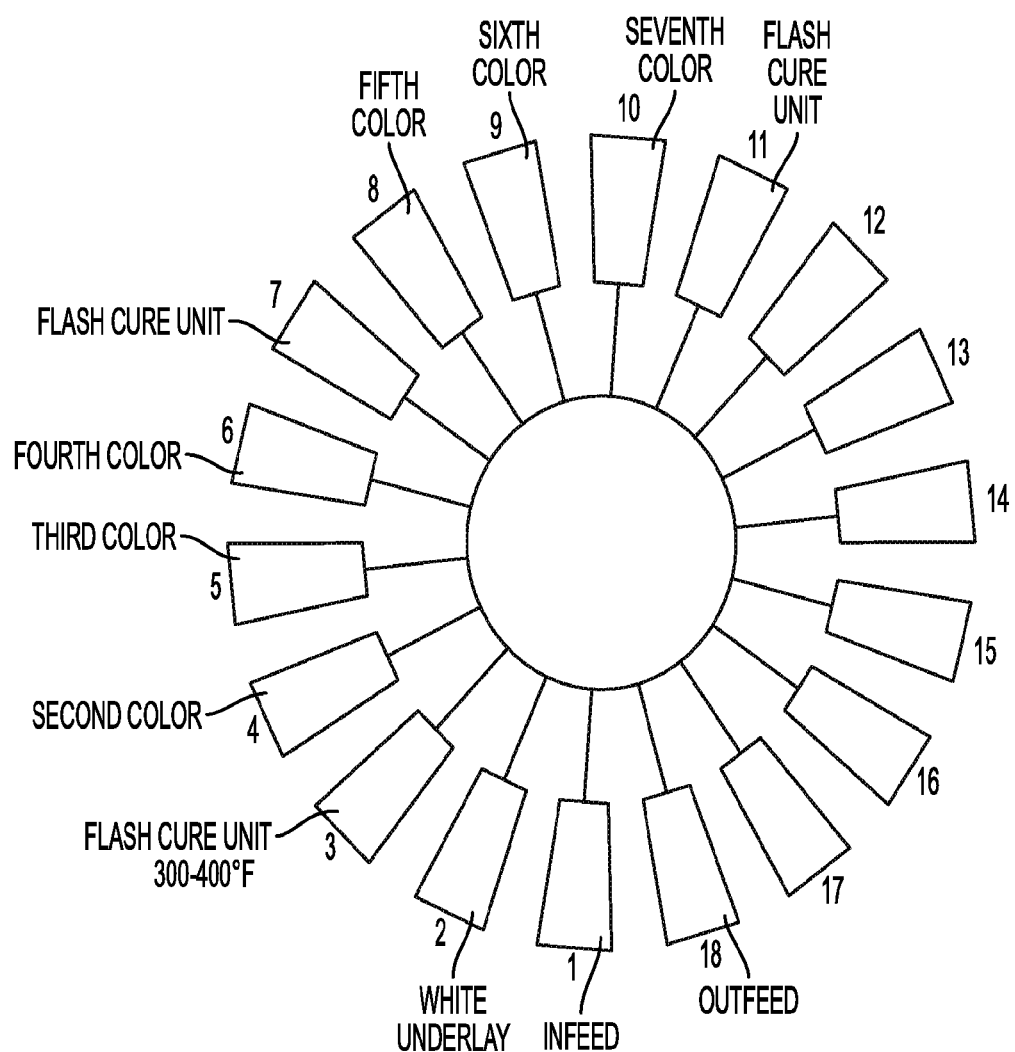

ULTRA LOW THERMO FUSION PVC PLASTISOL COATING AND TEXTILE PRINTING INK

CROSS-REFERENCE TO RELATED APPLICATIONS

This application claims priority under 35 U.S.C. § 119(e) to U.S. Provisional Patent Application Ser. No. 62/344,136, filed on Jun. 1, 2016, which is hereby incorporated by reference in its entirety.

FIELD OF THE INVENTION

The present disclosure relates to the field of plastisol, in particular, to a PVC plastisol that cures at temperatures lower than conventional compositions.

BACKGROUND OF THE INVENTION

Various existing plastisol are used for a variety of applications including surface coating for waterproofing, decorating, embellishing, as inks for screen printing designs on substrates such as textiles, for coating wires, cable and fishing lines, and for creating casts from molds. Typically, plastisol consists of PVC particles suspended in a liquid plasticizer with various other agents to achieve desired properties such as color, particle dispersion, and viscosity. At room temperature, they are in a liquid paste state and will not dry by evaporation. When heated to high temperatures of around 177 degrees Celsius (about 350 degrees Fahrenheit), the plastisol will cure and form a flexible permeant solid.

Typically, an automated screen printing press is used for commercial screen printing. The automated screen printing press consists of a series of stations arranged in a circle and a series of corresponding pallets. Each station may further consist of either a printing head or a flash cure unit. The pallets rotate along the circle, stopping at each station. The printing process begins by manually setting the substrate on a pallet at the first station using a temporary adhesive. The temporary adhesive prevents the substrate from shifting and moving during the printing process. The first plastisol ink is applied to the substrate. The pallet rotates to the second station. A flash cure unit cures or gels the ink. The flash cure unit heats the ink to around 177 degrees Celsius (about 350 degrees Fahrenheit). The operating temperature of the flash cure unit depends on the distance to the substrate, the duration of the cure, and the type of plastisol. Flash cures are required for multi-color print on light color and dark color substrates. Specifically, conventional processes have the following limitations: (1) Multi-Color Print on light color substrate needs flash cure every three or four print; (2) Multi Color Print on Dark Color (e.g. black, blue, brown, red, purple) substrates needs flash cure after the first color (normally, white or grey) print as underlay and thereafter every three or four color print in order to prevent excessive ink absorption into substrate(reducing opacity effect) and ink migration into other color or colors, build-up ink on print side of screen and increase opacity. After the flash cure, sufficient time is required to cool off heated plate, ink and substrate to prevent ink migration, blocking screen by ink build-up, and other problematic issues. This is accomplished by either rotating two or three plates (stations) without printing process or incorporating a cooling mechanism such as a fan. Once cooled, the next station can apply the second color. The process of applying ink, flash curing, and cooling repeats for other ink color or colors. At final station, the substrate with the completed design print is manually transferred to a conveyor dryer.

The conveyer dryer consists of a conveyor belt and a heating chamber. The product is placed on the conveyor belt and passes through the heating chamber. Referring to FIG. 2, typically, the heating element temperature of the electrical conveyer dryer is 540 degrees Celsius (1000 degrees Fahrenheit) to achieve temperatures between 93-170 degrees Celsius (200-340 degrees Fahrenheit) at the surface of the substrate. Alternative, gas-fired vortex belt dryers achieve substrate surface temperatures of between 150 and 180 degrees Celsius (300-360 degrees Fahrenheit).

The high temperature required to cure and dry PVC plastisol presents a number of problems well-known in the industry. The heat causes the PVC to release toxic hydrogen chloride gas which poses an occupational hazard to those working with PVC plastisol. The high temperature also requires high energy consumption which places a burden on producers, energy providers, and the environment. The high temperature also precludes the use of heat-sensitive substrates including but not limited to acrylic, polyester, spandex, nylon, polypropylene, artificial leather, and rubber. Heat-sensitive substrates currently require solvent-based compositions which are costlier to manufacture than PVC plastisol, potentially toxic, and contain large volumes of volatile organic compounds (VOC) which pose environmental risks, including contributing to climate change.

In addition, the high temperature increases mechanical stress and causes the plastisol to deform. It also degrades the adhesives used to keep substrates in place during the plastisol ink application. This requires the liberal use of expensive and potentially toxic heat-resistant adhesives. The high temperature (higher than water boiling point) also causes disperse dye thermo-migration(sublimation) by decomposing dyes and bleed into the plastisol. This permanently discolors the plastisol. To counter this, the plastisol may be made more viscous, which makes working with the plastisol more difficult. Alternatively, expensive high-energy dyes less susceptible to dye sublimation can be used.

The high temperature also requires more cooling between applications and before handling. This requires more time and expensive and large equipment to facilitate cooling including intermediate cooling stations between applications and conveyor belt dryers after final application.

Currently existing methods of producing low-temperature curing PVC plastisol have problems such as short shelf-life which render them commercially non-viable or require more frequent or longer flash curing.

In addition to the problems associated with high temperature curing, currently available plastisol requires the addition of a bonding agent in order to adhere to some substrates such as hydrophobic and crystallized substrates. The plastisol with bonding agents have a short shelf-life and may discolor the plastisol. In addition, currently available plastisol has a lower surface tension than the substrates which can results in poor coverage on the substrates. They are also brittle and stiff once cured.

Also, when currently available PVC plastisol-based products are disposed and incinerated, they release the toxic hydrogen chloride gas again.

Therefore, a need exists for an improved and environmentally friendly PVC plastisol.

SUMMARY OF THE INVENTION

The present invention meets such a need. Described herein is a novel plastisol composition formulated to replace current hazardous and toxic polyvinyl chloride plastisol by incorporating a unique combination of low temperature gelling and fusible plasticizers and polymer or polymers which will not start the elimination and formation of toxic agent (hydrochloride gas—HCl) from polymer or polymers and is also phthalate free. The new plastisol composition has a lower curing temperature than conventional plastisols and superior bonding and leads to denser coverage without de-wetting and crawling, and post-cure durability and water based ink like soft and thin feel. Further, due to the properties of very fast fusion at ultra low temperature, cooling in multicolor application would not be necessary, whereas for conventional classic PVC plastisol or other PVC free plastisol cooling down measures after flash cure are unavoidable. Furthermore, the product would not need flash cure thermal treatment one after another color deposit or printing. Because convey drier is no longer needed, the curing process for the present plastisol also saves energy and space. As a result, the plastisol of the present invention poses much less health risk and is more environmentally friendly.

The plastisol of the present invention also replaces solvent based and ultra-violet curable coating and ink used for coating and printing serigraphic medias and can be used on very thermal heat sensitive materials such as soft and hard vinyl, polyester, polyurethane (e.g. lycra or spandex), polypropylene woven or non-woven fabric. Carefully selected ingredients of new invented plastisol decrease crawling problem and deposit interruption and provide a flexible and soft touch feeling, as well as guarantee smooth and very dense deposit. The plastisol thus provides robust adhesion on every textile substrate without the addition of catalyst or bonding agent.

The plastisol maintain prolonged aged stable and creamy Newtonian viscosity without sharp increase instead of heavy pseudoplastic viscosity during storage period. Further, the plastisol contributes to static elimination without induction of moisture and provide very strong resistance to Ultra Violet and harsh weather.

The plastisol composition of the present invention includes:
(a) a first copolymer of vinyl chloride and vinyl acetate and optionally a second copolymer of vinyl chloride and vinyl acetate, wherein the mean particle size of the second copolymer is at least about 30% bigger than the mean particle of the first copolymer, and the ratio by weight between the first copolymer and the second copolymer ranges from about 4:1 to about 25:1 and
(b) a plasticizer mixture comprising at least three plasticizers selected from the group consisting of 2,2,4-trimethyl-1,3 pentanediol diisobutyrate, dioctyl terephthalate, dibutyl terephthalate, and benzyl butyl 1,2-cyclohexyldicarboxylate.

In some embodiments, the ratio between the total weight of the plasticizers and the total weight of the first and the second copolymers ranges from about 5:10 to about 9:10.

In some embodiments, less than about 5% by weight of the first copolymer is derived from vinyl acetate. In some embodiments, the mean particle size of the first copolymer is less than about 0.075 mm. In some embodiments, the mean particle size of the second copolymer is bigger than about 0.085 mm.

In some embodiments, the plasticizer mixture comprises 2,2,4-trimethyl-1,3 pentanediol diisobutyrate, and the ratio between the weight of the 2,2,4-trimethyl-1,3 pentanediol diisobutyrate and the total weight of the first and second copolymers ranges from about 1:200 and 1:10 by weight. In some embodiments, the plasticizer mixture comprises dioctyl terephthalate, and the ratio between the dioctyl terephthalate and the total weight of the first and second copolymers ranges from about 1:10 and 1:3 by weight. In some embodiments, the plasticizer mixture comprises benzyl butyl 1,2-cyclohexyldicarboxylate, and the ratio between the benzyl butyl 1,2-cyclohexyldicarboxylate and the total weight of the first and second copolymers ranges from about 1:10 and 1:6 by weight. In some embodiments, the plasticizer mixture comprises dibutyl terephthalate, and the ratio between the dibutyl terephthalate and the total weight of the first and second copolymers ranges from about 1:4 and 1:2 by weight.

The plastisol composition can further include at least one ingredient selected from the group consisting of a wetting agent, a dispersing agent, a cross-linking agent, a filler, a blowing agent, a rheology modifier, a thixotropic agent, a lubricant, an anti-static agent, a heat stabilizer, a pigment, a flame retardant, a foaming agent, a viscosity reducer, a dilatancy reducer, and an UV absorber.

In some embodiments, the wetting agent and/or dispersing agent is selected from the group consisting of an alkoxylate, a polar acidic ester, an anionic electrolyte, an acidic polyether, polydimethylsiloxane, a fluoro-substituted polyacrylate, and any combination thereof. In some embodiments, the crosslinking agent is selected from the group consisting of a peroxide, a tri-acrylate, and any combination thereof. In some embodiments, the filler is selected from the group consisting of calcium carbonate, alumina thrihydrate, micro sphere, silica, nepheline syenite, and any combination thereof. In some embodiments, the blowing agent is selected from the group consisting of an expandable microsphere, a copolymer of acrylate, and a combination thereof. In some embodiments, the rheology modifier and/or a thixotropic agent is silica. In some embodiments, the lubricant is selected from the group consisting of paraffin wax, polytetrafluoroethlene, and a combination thereof. In some embodiments, the anti-static agent is selected from the group consisting of an alkoxy titanate, an ammonium salt, and a combination thereof.

Another aspect of the invention provides a method of using the plastisol composition including (a) applying the plastisol composition to a substrate; and (b) exposing plastisol composition to a UV or heat source to cure the composition.

In some embodiments, the plastisol composition is exposed to the heat source at a temperature ranging from about 80° C. to about 115° C. In some embodiments, the plastisol composition is exposed to the heat source at a temperature of lower than about 120° C. In some embodiments, the plastisol composition is exposed to the heat source for less than about 10 seconds. In some embodiments, the plastisol composition is exposed to the heat source for less than about 5 seconds. In some embodiments, the substrate comprises a material selected from polyester, polyethylene, acrylic, polypropylene, natural or synthetic leather, polyamide, cotton, and any combination thereof. In some embodiments, the substrate is a textile substrate and the plastisol composition is printed on the substrate. In some embodiments, one or more additional plastisol compositions are printed on the substrate prior to step (b).

A related aspect provides a product manufactured according to the method described herein, wherein the product includes for example, printed textile (e.g. garment and cover) and coated substrates (e.g. tubing and auto parts).

These and other aspects of the present invention will be described in greater detail below.

BRIEF DESCRIPTION OF THE DRAWINGS

FIG. 1 shows description of printing processes of dark color substrate with plastisol ink with automatic printing machine (16 heads and 18 pallets) under low cure temperature for six or seven color printing

DETAILED DESCRIPTION OF THE INVENTION

Various embodiments of the present invention provide a novel plastisol composition which overcome the drawbacks of traditional ink. The advantages lie in the improved product quality and durability as well as reduced production cost. In particular, the printing process significantly cut down energy consumption and the generation of hazardous waste. A wide range of materials are suitable substrates for printing the composition of the present invention.

While the following text may reference or exemplify specific components of a composition or a method of utilizing the composition, it is not intended to limit the scope of the invention to such particular references or examples. Various modifications may be made by those skilled in the art, in view of practical and economic considerations, such as the weight percentage of a plasticizer and the temperature to cure the composition.

The articles "a" and "an" as used herein refers to "one or more" or "at least one," unless otherwise indicated. That is, reference to any element or component of the present invention by the indefinite article "a" or "an" does not exclude the possibility that more than one element or component is present.

The term "about" as used herein refers to the referenced numeric indication plus or minus 10% of that referenced numeric indication. For example, the term "about" appears in the description of percentage weights of plasticizers because the weights are only approximations and will vary depending upon the specific compositions and the application thereof. Even though the limits that define the present weight percentage of the plasticizers may be approximate, selecting a value within these ranges will enable one skilled in plastisol formulation to prepare of desirable viscosity plastisols with a minimum of experimentation.

The term "plastisol" as used herein refers to a liquid polymer composition comprising a particulate form of a polymer dispersed in a liquid phase comprising a plasticizer for the polymer. The present invention is not restricted to any particular polymer, although the invention may be described in terms of vinyl chloride polymers. The plastisol can include at least one non-crosslinked polymer.

The term "substantially free" means that a substance (e.g. phthalate plasticizer) is non-present in a plastisol composition, or the amount of the substance is so small that it does not impact the properties of the plastisol composition.

An aspect of the invention provides a plastisol composition which includes a first copolymer vinyl chloride and vinyl acetate and a plasticizer mixture containing 3 or more plasticizers. The combination of the multiple plasticizers is critical for curing at a low temperature and enhancing the tensile strength and the flexibility of the cured ink film. In addition, the cured ink film controls fiber fibrillation very well. There is a smooth and dense uniform layer on every substrate including for example untreated cotton garments.

Plasticizer

Plasticizers provide versatility to PVC and are key ingredients and tools for the vinyl formulator. They are used to adjust hardness (or softness), impart stain resistance, alter tensile properties (such as strength, elongation or flexibility) and processability as required for a multitude of applications, including without limitation flexible vinyl applications. While hundreds of plasticizers have been produced, only a few remain having acceptable performance properties when combined with vinyl or other polymeric materials. In some embodiments, the plasticizers of the plastisol described herein are substantially free of phthalates.

Plasticizers serve as a vehicle for the dispersion of resin (polymer) particles, such as PVC. The dispersion is initially a two-phase, heterogeneous system. Use of plasticizers in polymeric dispersions promotes the formation of homogeneous systems and polymer fusion occurs upon heating. The higher the solvating power, the lower the temperature at which a homogeneous system is fused, which, in turn, decreases the residence time and increases the speed at which polymeric compositions can be processed into an end product, resulting in a faster, more efficient and economical process.

In further examples, the intended function of the plasticizer in the fully gelled, plasticized polyvinyl chloride preparation is not only to provide the desired softness but also to have maximum resistance to migration into adjacent media. Further demands placed upon plasticizers result from the desire to avoid hazards to humans and the environment. It is no longer permissible in many countries to use the plasticizers di(2-ethylhexyl)phthalate, dibutyl phthalate and benzyl butyl phthalate in toys or baby items, or to use the plasticizers diisononyl phthalate, diisodecyl phthalate and di-n-octyl phthalate in toys or baby items which might enter children's mouths. There is therefore a particular requirement for suitable replacement materials for the abovementioned plasticizers di-(2-ethylhexyl) phthalate, dibutyl phthalate and benzyl butyl phthalate.

In view of these desirable function and the restrictions associated with plasticizers, it is important to adopt a generalized approach of minimizing or avoiding all phthalate-containing plasticizers in the production of plasticized polymers. The result of this is a requirement for phthalate-free plasticizers or new plasticizer combination which in terms of processability and service properties achieve the performance level of phthalate-containing plasticizers.

A combination or mixture of 2,2,4-trimethyl-1,3 pentanediol diisobutyrate, benzyl butyl 1,2-cyclohexyldicarboxylate, and one or more dialkyl terephthalates has been found to be important to a desirable gelling condition and an optimized product profile in terms of a low fusion/cure temperature, reduced fiber extrusion, improved tensile strength and other properties. One or more additional plasticizer can be included in the combination to further modify the manufacturing condition and the product profile. The ratio by weight between each individual plasticizer in the combination and the first polymer ranges from about 1:2 to about 1:25. Exemplary ratios include about 1:3, 1:4, 1:5, 1:6, 1:7, 1:8, 1:9, 1:10, 1:15 and 1:20.

Each of the alkyl group in the dialkyl terephthalate can be independently a liner or branched and substituted or unsubstituted C1-C15 alkyl group, such as methyl, ethyl, propyl, butyl, isobutyl, pentyl, isopentyl, hexyl, heptyl, octyl, and isomers and analogs thereof. Examples include dibutyl terephthalate and dioctyl terephthalate.

The plasticizers can be prepared according to chemistry procedure known in the field or can be obtained from a commercial source. For example, the preparation of a dialkyl terephthalate is within the skills of one of ordinary skill in the art through coupling reactions between a dibenzoic acid and an alcohol. Plasticizers such as TXIB, Santicizer 278, Santicizer 375, Platinum P-1400, Effusion, Platinum P-1700, and Polysorb are also available from comerical sources.

In further examples, the plasticizer combination includes a dibenzoate such as DEGDB, DPGDB, and 1,2-propylene glycol dibenzoate (PGDB). Other examples include monobenzoates (derived from benzoic acid and a monohydric alcohol such as 2-ethylhexanol, isooctanol or isononanol), monobenzoates of diols, glycols and ethers of glycols containing from 2 to 8 or more carbon atoms, and commercially available esters of diols, such as the mono- and diisobutyrates of 2,2,4-trimethyl-1,3-pentanediol.

Various compounds are suitable substitute for phthalates. As the plasticizer, straight-chain dibasic acid esters can be used such as a dioctyl adipate (DOA), a dioctyl azelate (DOZ), and a dioctyl sebacate (DOS). As the plasticizer, phosphoric acid ester series may be used such as a tricresyl phosphate (TCP), a trioctyl phosphate (TOF), a trixylenyl phosphate (TXP), a monooctyl diphenyl phosphate, and a monobutyl-dixylenyl phosphate (B-Z-X). As the plasticizer, benzoic acid ester series can be used such as tri(2-ethylhexyl) trimellitate (TOTM), a tri-n-octyl trimellitate, a triisodecyl trimellitate, a tri-iso-octyl trimellitate. As the plasticizer, esters can be used such as a tributyl citrate ester, a trioctyl-acetyl citric acid ester, a trimellitic acid ester, a citric acid ester, a sebacic acid ester, an azelaic acid ester, a tri- or tetraethylene glycol ester of maleate $C_6$-$C_{10}$ fatty acid, an alkyl sulfonic acid ester, and a methyl acetyl ricinoleate. The plasticizer may be an saturated fatty acid glyceride such as a soybean oil having double bonds thyereof epoxidized with a hydrogen peroxide or a peracetic acid, that is, en epoxidized soy bean oil (ESBO), too. The plasticizer may be an epoxidized vegetable oil such as an epoxy compound of an alkyl oleate ester or the like of butyl or octyl, or a viscous low polymerization degree polyester of an average molecular weight of about 500 to 8000 having a straight chain of propylene glycol ester units of a dibasic acid such as an adipic acid (e.g. an adipic acid polyester, a phthalic acid-based polyester) or the like, too. As the plasticizer, one of them may be used alone or two or more of them may be used in appropriate combination. In some embodiments, the plastisol composition does not contain a phthalate as a plasticizer.

In some embodiment, the plasticizer combination contains a phthalate as a plasticizer. Among them, the phthalic ester is one of the most common plasticizers and is easy to be procured, thereby contributing to cost reduction. Moreover, the phthalic ester is capable of dispersing the vinyl chloride resin still more uniformly, thereby forming a stable vinyl chloride plastisol. Particularly, from the viewpoint of elimination of an environmental load, ease of handling, solubility, coating property, storage stability and so on, the diisononyl phthalate (DINP) or the dioctyl phthalate (DOP) is used most commonly among the phthalates.

In some embodiments, the plasticizer combination includes 2,2,4-trimethyl-1,3 pentanediol diisobutyrate, dioctyl terephthalate, dibutyl terephthalate, and benzyl butyl 1,2-cyclohexyldicarboxylate. In some embodiments, the plasticizer combination includes 2,2,4-trimethyl-1,3 pentanediol diisobutyrate, dioctyl terephthalate, dibutyl terephthalate, benzyl butyl 1,2-cyclohexyldicarboxylate, 1,2-benzenedicarboxylic acid-1,2-benzenedicarboxylic acid-2,2-dimethyl-1-(1-methylethyl)-3-(2-methyl-1-oxoropoxy) propyl phenylmethyl ester, and one, two or more commercial plasticizers selected from Santicizer 375, Santicizer 278, platinun p-1700, and polysorb (isosorbide-biobased plasticizer: e.g. Polysorb ID 46). In some embodiments, the plasticizer combination includes 2,2,4-trimethyl-1,3 pentanediol diisobutyrate, dioctyl terephthalate, dibutyl terephthalate, benzyl butyl 1,2-cyclohexyldicarboxylate, 1,2-benzenedicarboxylic acid-1,2-benzenedicarboxylic acid-2,2-dimethyl-1-(1-methylethyl)-3-(2-methyl-1-oxoropoxy)propyl phenylmethyl ester (commercially available as Santicizer 278), and Polysorb ID 46 (isosorbide-biobased plasticizer, manufactured by Roquette).

The above described plasticizers can be used individually and in blends with other plasticizers in applications that include but are not limited to: adhesives, caulks, architectural coatings, industrial coatings, OEM coatings, other types of plastisols, sealants, overprint varnishes, polishes, inks, melt compounded vinyl, polysulfides, polyurethanes, epoxies, styrenated acrylics and combinations thereof. Other applications will be evident to one skilled in the art based upon the disclosure herein.

Polymer

Any of the known polymers that can be formulated into a plastisol can be used to prepare low viscosity plastisols in accordance with the present invention. The polymers constituting the dispersed phase of the present plastisols include polymers of ethylenically unsaturated organic monomers and mixtures of these monomers that can be prepared by a free radical-initiated emulsion polymerization. Suitable monomers include but are not limited to 1) ethylenically unsaturated halocarbons such as vinyl chloride, 2) ethylenically unsaturated acids such as acrylic and methacrylic acids and esters thereof with alcohols containing up to eight or more carbon atoms, and 3) copolymers of vinyl alcohol with olefins such as ethylene and vinyl acetate.

As the vinyl monomer to be copolymerized with the vinyl chloride or the vinylidene chloride, there may be used vinyl esters such as a vinyl acetate, a vinyl propionate or a vinyl stearate, vinyl ethers such as a vinyl methyl ether or a vinyl isobutyl ether, maleic acid esters such as a diethyl maleate or the like, fumaric acid esters such as a dibutyl fumarate, (meth)acrylic acid alkyl esters such as a methyl acrylate, an ethyl acrylate, a 2-ethylhexyl acrylate, 2-hydroxyethyl acrylate, hydroxyalkyl esters of acrylic acid or methacrylic acid such as 2-hydroxyethyl acrylate, 2-hydroxyethyl methacrylate, a hydroxypropyl acrylate, a hydroxypropyl methacrylate, hydroxyalkyl amides of acrylic acid or methacrylic acid such as a N-methylol acrylamide, a N-methylol methacrylamide, a N-hydroxyethyl acrylamide, a N-dihydroxyethyl methacrylamide, an acrylonitrile or the like. They may be copolymerized with the vinyl chloride generally at a rate of less than about 40%, less than about 30%, less than about 20%, less than about 10%, or less than about 5% by weight (wt %). Among them, the vinyl acetate is preferred as the monomer to be copolymerized with the vinyl chloride or vinylidene chloride, from the viewpoint of a swelling/gelling property to a plasticizer or a high adhesion to a metal surface. Moreover, the rate of the vinyl acetate to be copolymerized is preferably less than about 10%, less than about 5% or less than about 3% from the viewpoint of the storage stability, water resistance, chemical resistance and the like. The vinyl chloride may also be a crosslinkable copolymer having a suitable crosslinking group. Furthermore, as such vinyl chloride resin, one kind of vinyl chloride resin may be used alone, or two or more kinds of vinyl chloride resins may be used in appropriate combination.

The vinyl chloride resin preferably has an average degree of polymerization in the range of 500 to 2500, more preferably in the range of 850 to 2000, and still more preferably in the range of 1000 to 1900, from the viewpoint of obtaining a high storage stability, a good chipping resistance and a tough coating property.

In some embodiments, the first copolymer of vinyl chloride and vinyl acetate has a mean particle size of less than about 0.075 mm. Other exemplary mean particle sizes for the first copolymer include less than about 0.070 mm, less than about 0.065 mm, less than about 0.060 mm, less than about 0.055 mm, less than about 0.050 mm, less than about 0.045 mm, and less than about 0.045 mm. Vinyl acetate contributes to about 1%, about 2%, about 3%, about 4%, about 5% or about 6% of the copolymer. The copolymer can be prepared according to the requirements of the target composition or obtained from a commercial source (e.g. Vinnolit PA 5470/5).

The first copolymer can be used in combination with a second polymer. The second copolymer has a bigger mean particle size than the first copolymer and provides a number of advantages including reduced viscosity, optimized bonding and mechanical performance of the product, and regulated surface gloss.

The mean particle size or diameter of the second copolymer is at least about 35%, at least about 30%, at least about 25%, at least about 20%, at least about 15%, or at least about 10% bigger than the mean particle size or diameter of the first copolymer. The ratio by weight between the first copolymer and the second copolymer ranges from about 70:30 to about 99:1. Other exemplary ratios by weight between the first copolymer and the second copolymer include about 75:25, about 80:20, about 85:15, about 90:10, and about 95:5. Further examples of the ratio by weight between the first copolymer and the second copolymer include from about 4:1 to about 35:1, from about 5:1 to about 25:1, from about 5:1 to about 20:1, from about 5:1 to about 10:1, and from about 3:1 to about 4:1.

In some embodiments, the second polymer is a copolymer of vinyl chloride and vinyl acetate. In some embodiments, the second copolymer has a mean particle size of bigger than about 0.060 mm, bigger than about 0.065 mm, bigger than about 0.070 mm, bigger than about 0.075 mm, bigger than about 0.080 mm 0.085 mm, bigger than about 0.090 mm or bigger than about 0.100 mm.

Each of the copolymer can have a functional group for cross-linking. Exemplary groups include epoxy group, amino group, hydroxyl and carboxy group.

Other Components/Ingredients

The plastisol composition can include at least one ingredient selected from a wetting agent, a dispersing agent, a cross-linking agent, a filler, a blowing agent, a rheology modifier, a thixotropic agent, a lubricant, an anti-static agent, a heat stabilizer, a pigment, a flame retardant, a foaming agent, a viscosity reducer, a dilatancy reducer, and an UV absorber.

The wetting agent can serves the role such as reducing liquid surface tension, minimizing foaming, improving colorant acceptance, facilitating ink transfer, and improving ink adhesion. Each of the wetting agent generally account for about 0.1% to about 5% of the plastisol composition and is often available from a commercial source. For example, commercially available Hydropalat WE 3650 (modified alkoxylate), CoatOSil 1211 (organomodified polydimethylsiloxane) or Afcona 3700 (fluoro-substituted polyacrylic polymer) can be used as a wetting agent and surface tension modifier.

The dispersing agent serves to prevent flocculation of particles by adsorbing on the solid-liquid interface and assuring repulsion between the particles. Examples of dispersing agents include polar acidic ester, anionic electrolyte, acidic polyether, oragno-phosphate compound, polydimethylsiloxane, and a fluoro-substituted polyacrylate. Commercially available dispersing agents include, for example, Disperplast 1142, Disperplast 1150, BYK 1161, Dispex AA 4144, and EFKA FA 4620. Each of the dispersing agent is from about 0.1% to about 5%, or from about 1% to about 3% of the plastisol composition and can be used alone or in combination.

The selection of a cross-linking agent depends on the functional group of the polymer. For example, acidic phosphates, triazines, polyamines, polyamides and the like are used when the polymer particles have an epoxy group as a functional group; polycaboxylates, polyepoxides and the like are used when the polymer particles have an amino group as a functional group. On the other hand, polyisocyanate compounds are used when the polymer particles have a hydroxyl group as a functional group; and polyamides, polyamines, polyepoxides and the like are used when the polymer particles have a carboxyl group as a functional group. Further examples include 1,1-di(tert-amylperoxy) cyclohexane and trimethylolpropane triacrylate. Various agents are commercially available such as TRIGONOX 122-C80 and LUPEROX 531M180. Each of the agents can be used alone or in combination and the amount of each agent is about 1% to about 5% of the polymer by weight.

A filler can serve multiple functions such as reducing the usage of titanium dioxide or plasticizer, maintaining a desirable viscosity and increasing opacity. Exemplary fillers include precipitated calcium carbonate, calcium carbonate, calcium carbide such as precipitated calcium carbide, or ultrafine calcium carbide; magnesium carbide; silicates such as silica, talc, diatomaceous earth, clay, and mica; alumina such as alumina trihydrate; expanded micro sphere; glass sphere; microcrystalline silica; and nepheline syenite (about 5-15 microns), and any combination thereof. The fillers can be used alone or in combination with each other and each is about 0.1% to about 45%, about 1% to about 40%, about 1% to about 35%, about 1% to about 30%, about 5% to about 20%, about 5% to about 15%, or about 5% to about 10% of the entire plastisol composition. In some embodiments, each of the fillers is about 1% to about 50%, about 1% to about 40%, about 1% to about 35%, about 1% to about 30%, about 1% to about 20%, about 1% to about 10%, about 5% to about 20%, about 5% to about 15%, or about 5% to about 10% of the plastisol base consisting of plasticizers, wetting & disperse agent, and polymer or polymers.

A blowing/foaming agent is capable of producing a cellular structure via a foaming process in a material such as a polymer that undergo hardening or phase transition. The cellular structure in a matrix can reduce density, increasing thermal and acoustic insulation. The agent can be a physical or a chemical agent or a combination of both types of agents. Inorganic agents include sodium borate, and sodium hydrogen carbonate, and organic agents include azodicarboxamide, P,P'-oxybis(benzenesulfonylhydrazide), and N,N'-dinitroso-N,N'-dimethyleterephthalamide. In some additional embodiments, the blowing agent includes a thermal expandable microsphere and/or a polymer. The polymer can be a single or copolymer of any two or three of acrylonitrile, methacrylonitrile and methyl methacrylate (e.g, a copolymer particle of about 15 to about 25 microns. Each individual component of the blowing agent is about 0.2% to about 5% of the plastisol composition by weight. The agent can be commercially available such as MS-140 DS and Expancel 031DU.

A rheology agent and/or a thixotropic agent serves to improve uniformed film monolayer, prevent undesirable flow, and reduce sedimentation. Silica such as treated or untreated fumed silica and pyrogenic silica are suitable agents for such purpose. The amount of the agent is generally about 0.1% to about 1% of the plastisol composition by weight.

A lubricant can help with reducing heat build-up during manufacturing process and preventing gelling during printing. Examples include polytetrafluoroethlyene and crystalline parafinwax. The amount of the agent is generally about 1% to about 5% of the plastisol composition by weight. Commercial agents include SST-4D with about mean particle size of about 3 microns.

The use of an anti-static agent prevent or diminish surface electricity by reducing the surface resistivity. In addition, it can reduce moire phenomenon and prevent interruption of smooth and uniformed layer deposit. The amount of the agent is generally about 1% to about 5% of the plastisol composition by weight. Examples include neoalkoxy titanate and dodecylethyldimethylammonium ethyl sulphate. Commercial agents include KS N-100 and EFKA 6780.

An emulsifier can also be used in the plastisol composition. Examples of the emulsifier include alkyl sulfate salts such as sodium lauryl sulfate and sodium myristyl sulfate; alkylaryl sulfonate salts such as sodium dodecylbenzenesulfonate, and potassium dodecylbenzenesullfonate; sulfosuccinate salts such as sodium dioctyl sulfosuccinate, sodium dihexyl sulfosuccinate; fatty acid salts such as ammonium laurate, and potassium stearate; anionic surfactants such as polyoxyethylene alkyl sulfate salts, and polyoxyethylene alkylaryl sulfate salts; sorbitan esters such as sorbitan monooleate, and polyoxyethylene sorbitan monostearate; monionic surfactants such as polyoxyethylene alkyl ethers, and polyoxyethylene alkylphenyl ethers; cationic surfactants such as cetylpyridinium chloride, and cetyltrimethylammonium bromide; as well as styrene/maleic acid copolymer ammonium slat; and the like. an emulsifier may be used singly, or used in combination with two or more emulsifiers.

These emulsifiers may be used singly, or two or more of them may be used in combination. The amount of the emulsifier may be usually 0.05 to 5 parts by weight, preferably 0.2 to 4.0 parts by weight, per 100 parts by weight of the monomer used.

As the viscosity modifier, there can be cited, for example, solvents such as xylene, solvent naphtha, mineral spirit, methyl isobutyl ketone, and butyl acetate, and suitable surfactants. Additional agents for reducing viscosity and/or dilatancy include 1-dodecene and carboxylic acid derivatives, which are commercially available such as Viscobyk 4015 and 5025. The agent weighs about 1-10% of the weight of the polymer.

Thermal stabilizers are optional as the cure temperature is significantly reduced. Examples of the thermal stabilizer include metal soaps such as magnesium stearate, aluminum stearate, calcium stearate, barium stearate, zinc stearate, calcium laurate, barium laurate, and zinc alurte; organotin compounds such as dibutyltin dilaurate, dibutyltin dimaleate, and monobutyltin mercaptide; phosphorous acid esters such as diethyl phosphite, dibutyl phosphite, dioctyl phosphite, diphenyl isodecyl phosphite, tricresyl phosphite, triphenyl phosphite, tris(nonylphenyl) phosphite, and triisooctyl phosphite; and the like.

Pigments are chosen for stability and color-fastness on the substrate to be imaged. Pigments are particulate in form, which is a consideration on proper dispersion of such solids in the plastisol compositions of the present invention. Therefore, some care should be taken to provide adequate mixing of the ingredients of the plastisol ink composition. Pigments are as varied as the colors of desired by the consumer. Pigments are well known to those of skill in the art, and are not different from pigments useful in the plastisol ink compositions containing polyvinyl halides and phthalates.

Application of Plastisol Composition

Although the exemplified application illustrate printing the plastisol composition on apparels, the present invention is certainly not limited to such application. the plastisol composition can be applied to various fields including for example plastisol coating, molding, tubing, thermoforming, flooring covering, rust prevention coating, construction, anti-tripping, rust preventing, medical products, cable insulation & coating, textile decorating and ink printing, serigraphic ink printing, and consumable products. The substrate where the plastisol composition is applied includes for example, synthetic leather, wall paper, water proof sheet, floor tile, floor carpet backing, floor cushion, building materials, roofing tile, guttering, window frame, automotive air & oil filter, car seat, blood bag & intravenous line, feeding tube, parts of dialysis, apparels, tarpauline and stretch wrap, food container, bottle, hoses, curtains and many other woven or nonwoven, textile or natural or synthetic materials. The materials can be made from for example polyester, soft vinyl material substrate, acrylic, polypropylene non-woven, artificial leather, nylon (polyamide), cotton and any combination thereof.

In addition to printing applications on textiles such as cotton, acrylic, polyester, Spandex (Lycra) and nylon, printing is also possible on polypropylene, soft and hard PVC, artificial leather, rubber, etc. More specific applications include plastisol coating and molding, calendaring, glove and tool dipping, textile, natural and synthetic leather coating and toy-slash molding. In the flooring covering industries, the non-PVC plastisol can be applied to floor tile, floor carpet backing and floor cushions. For sheets and coverings, the non-PVC plastisol could be applied to synthetic leather, wall paper and sheets for water proofing. Applications are also available for building materials, roofing tile, guttering and window frames. Rust prevention is also possible by using the non-PVC plastisol for coating. In the automotive industry, the non-PVC plastisol could be applied to under body coating for anti-tripping, rust prevention and splash noise dumping, as a sealing compound, spot welding, air and oil filters, car seats, etc. The non-PVC plastisol could also be used for medical products in applications for blood bags and IV tubing. Other applications include cable insulation and coating, textile decorating and printing ink for children's wear, garments, t-shirts, pajamas, underwear at the like. Applications in serigraphic printing ink and packing materials such as tarpauline, stretch wrap, food containers, bottles and the like are also available. The PVC alternative plastisol provides superb resistance of disperse dye thermomigration phenomenon (dye bleeding caused by dye sublimation) for disperse dye dyed man-made substrates. It minimizes the effect from bleeding by maintaining fusion temperature much lower than normal starting temperature.

Due to the properties of very fast fusion at low temperature, heat cooling down steps in multicolor application would not be necessary as in conventional classic PVC Plastisol or other PVC free plastisol, where heat cooling down measures are unavoidable after flash cure. Furthermore, this product would not need flash cure thermal treatment one after another color deposit or printing.

The method of using plastisol composition of the present invention generally involves applying the composition to a substrate and allows the composition to cure at a suitable temperature within a reasonable period of time. The means of application depends on the intended filed of use and the specific substrate. Exemplary approaches include screen printing, molding, and dipping. More specific methods include for example extrusion, calendaring, injection molding, rotational molding, dip molding, slush molding, coating, textile printing.

The temperature for curing the plastisol composition can vary depending on factors such as the components and the target use of the composition. In some embodiments, the cure temperature ranges from about 50° C. to about 300° C., from about 50° C. to about 250° C., from about 50° C. to about 200° C., from about 50° C. to about 150° C., from about 50° C. to about 100° C., from about 60° C. to about 100° C., from about 60° C. to about 90° C., from about 60° C. to about 95° C., from about 75° C. to about 250° C., from about 75° C. to about 200° C., from about 75° C. to about 150° C., from about 75° C. to about 100° C., from about 85° C. to about 100° C., from about 80° C. to about 115° C., from about 82° C. to about 115° C., from about 85° C. to about 150° C., from about 85° C. to about 200° C., from about 85° C. to about 150° C., from about 85° C. to about 100° C., from about 100° C. to about 300° C., from about 100° C. to about 250° C., from about 100° C. to about 200° C., from about 100° C. to about 150° C., from about 150° C. to about 300° C., from about 150° C. to about 250° C., from about 150° C. to about 200° C., from about 200° C. to about 300° C., from about 200° C. to about 250° C., from about 250° C. to about 300° C., from about 30° C. to about 50° C. In further exemplary embodiments, the cure temperature is lower than about 500° C., lower than about 450° C., lower than about 400° C., lower than about 350° C., lower than about 300° C., lower than about 250° C., lower than about 200° C., lower than about 150° C., lower than about 115° C., lower than about 100° C., lower than about 90° C., lower than about 80° C., lower than about 70° C., lower than about 60° C., lower than about 50° C., or lower than room temperature. Heating, IR and UV radiation can also be used individually or in combination, at the same time or sequentially for curing a composition. Unless otherwise specified, the cure temperature is measured at the surface of the plastisol composition applied to the substrate. The temperature achieved at such surface determines the curing result.

The length of time for curing can vary depending on the specific composition, the substrate, and other relevant factors. Exemplary lengths of time include less than about 100 seconds, less than about 80 seconds, less than about 60 seconds, less than about 50 seconds, less than about 40 seconds, less than about 30 seconds, less than about 20 seconds, less than about 15 seconds, less than about 10 seconds, less than about 8 seconds, less than about 6 seconds, less than about 4 seconds, less than about 3 seconds, and less than about 2 seconds. In some further embodiments, the time for curing takes about 1, about 2, about 3, about 4, about 5, about 6, about 7, about 8, about 9, about 10, about 15, about 20, about 25, about 30, about 40 seconds. In some exemplary embodiments, the cure condition requires heating at about 80°-115° C. for about 10 to about 30 seconds. In some embodiment, the curing requires heating at about 450° C. for about 3 to about 5 seconds. In some exemplary embodiments, the cure condition requires heating at a temperature of lower than about 100° C. for less than about 10 seconds. In some embodiment, the curing requires heating at about 450° C. for about 3 to about 5 seconds. In some embodiments of curing, the applied plastisol composition is exposed to the heat source at a temperature ranging from about 80° C. to about 115° C. for less than about 10 seconds or less than about 5 seconds. In some embodiments of curing, the applied plastisol composition is exposed to the heat source at a temperature lower than about 115° C. for less than about 10 seconds or less than about 5 seconds.

A composition can be cured in a single stage or over multiple stages. Multiple plastisol compositions with the same or different colors can be applied to a substrate at the same time or sequentially. In some embodiments, two, three, four, five, six, seven, eight, nine, ten or more compositions are applied sequentially or at the same time to a substrate before the compositions are being subject to a curing condition (e.g. flash heating). Therefore, the cooling step between curing individual compositions is not necessary in the present invention.

EXAMPLES

Example 1

A PVC plastisols was blended in dual shaft disperser or triple shaft disperser at room temperature or 16° C. for approximately 15-35 minutes using following procedure: the liquid additives were dispersed in the combination of plasticizers, then the polymers and extender were introduced and mixed for 5-10 min and then the solid and other liquid additives were mixed. The mixing was continued for 5-10 min. The rheology modifier was then added and the blending continued for 5 minutes.

When a plasticizer or plasticizers, a polymers, and a filler were combined in blending mixer, heat started to build up due to friction of components to about 32° C. or higher. The elated temperature and mechanical stress could accelerate plastisol gelation and affect their mechanical properties, dimensional stability and other properties (e.g. viscosity, printability, processability, and aged stable shelf life). Therefore, in order to minimizing heat build-up of plastisol compound, appropriate measures and equipment should be adopted such as using water jacketed double wall mixing tank, or adding polymer into the plasticizer or plasticizers at same time. Alternatively, by adding the polymer first or using less plasticizer, heat buildup can be kept under control.

The composition of a plastisol is illustrated as follows:

| | | |
|---|---|---|
| A. | plasticizers - non-phthalate polymer modifiers | |
| | 1 dioctyl terephthalate (e.g Eastman 168) | 20-60% of polymer[a] |
| | 2. dibutyl terephthalate (e.g Eastman Effusion) | 20-60% of polymer[a] |
| | 3. benzyl butyl 1,2-cyclohexyldicarboxylate | 10-30% of polymer[a] |
| | 4. 1,2-benzenedicarboxylic acid-1,2-benzenedicarboxylic acid-2,2-dimethyl-1-(1-methylethyl)-3-(2-methyl-1-oxoropoxy)propyl phenylmethyl ester) | 5-20% of polymer[a] |
| | (total weight of plasticizer 1, 2, 3 and 4 is 60-80% of polymer) | |
| B. | coupling agent | 0.1-0.6% of polymer[a] |
| C. | wetting agent | 0.1-2% of TFM[b] |
| D. | disperse agent | 0.1-2% of TFM[b] |

-continued

| | | |
|---|---|---|
| E. | crosslinking & coupling-agent | 0.1-4% of polymer[a] |
| F. | deaerator | 0.1-1% of TFM[b] |
| G. | prepared pigment toners | 1-40% of TFM[b] |
| H. | filler - precipitated calcium carbonate | 5-40% of Base[d] |
| I. | blowing agent copolymer/isobutane | 0.5-3% of TFM[b] |
| J. | heat stabilizer | 1 to 3% of polymer[a] |
| K. | flexbilizer non-caboxylated butadiene acrylonitrile copolymer latex | 0.5-1% of TFM[b] |
| L. | polyvinyl chloride polymers | |
| | 1. homopolymers VINNOLIT E70TT | 10-100 parts |
| | 2. homopolymer VINNOLIT EP 6060 | 10-50 parts |
| | 3. suspension homopolymer: VINNOLIT C 65C or C65W | 10-20 parts |
| | 4. copolymer VINNOLIT PA 5470/5 | 10-100 parts |
| | (Total parts of single use or combination of the above 4 polymers: 100 parts)[c] | |
| M. | rheology modifier | 5-10% of polymer[a] |
| N. | anti-static agent | 1-5% of TFM[b] |

[a] the percentage value refers to the weight of the individual plasticizer relative to the weight of the polymer(s);
[b] the percentage value refers to the weight of the individual agent relative to the total formulation weight (TFM) of the plastisol composition;
[c] the total amount of the polymer or polymers is about 10-70% of the total formulation weight (TFM) of the plastisol composition;
[d] The Base consists of the plasticizers, the wetting agent, the dispersing agent, coupling agent, and the polymer(s).

Example 2

Using procedures similar to those in Example 1, a second plastisol composition includes the following components:

| | | |
|---|---|---|
| A. | plasticizers - non-phthalate polymer modifiers | |
| | 1. dioctyl terephthalate (e.g. eastman 168) | 30-60% of polymer[a] |
| | 2. dibutyl terephthalate (e.g. eastman effusion) | 30-60% of polymer[a] |
| | 3. benzyl butyl 1,2-cyclohexyldicarboxylate | 10-30% of polymer |
| | 4. plasticizer (platinum p-1700) | 30-50% of polymer[a] |
| | (total weight of plasticizer 1, 2, 3 and 4 is 60-80% of polymer) | |
| B. | wetting agent hydropalat we 3650 | 0.1-2% of TFM[b] |
| C. | dispersing agent efka 4670 | 0.1-2% of TFM[b] |
| D. | crosslinking & co-agent trigonox 122-c80 | 0.1-4% polymer[a] |
| E. | defoamer efka pb 2744 | 0.1-1% TFM[b] |
| F. | prepared pigment toners | 5-15% of TFM[b] |
| G. | filler - precipitated calcium carbonate socal s-322 | 0-50% of base[d] |
| H | blowing agent copolymer/isobutane expancel 031DU | 0.5-3% of TFM[b] |
| I. | heat stabiizer plas-check 775 | 1 to 3% of polymer[a] |
| J. | flexibizer non-caboxylated butadience acrylonitrile copolymer. latex (nychem 1552) | 0.5-1% of TFM[b] |
| K. | polymers | |
| | 1. homopolymer vinnolit E70 TTt | 10-50 parts |
| | 2. homopolymer vinnolit EP 6060. | 10-50 parts |
| | 3. suspension homopolymer: vinnolit c65c or c65w | 10-20 parts |
| | 4. copolymer vinnolit pa 5470/5 | 10-100 parts |
| | (Total parts of single use or combination of the above 4 polymers: 100 parts)[c] | |
| L. | rheology modifier santicizer 375 | 5-10% of polymer[a] |
| M. | anti-static | 1-5% of TFM[b] |

[a] the percentage value refers to the weight of the individual plasticizer relative to the weight of the polymer(s);
[b] the percentage value refers to the weight of the individual agent relative to the total formulation weight (TFM) of the plastisol composition;
[c] the total amount of the polymer or polymers is about 20-70% of the total formulation weight (TFM) of the plastisol composition;
[d] The base consists of the plasticizers, the wetting agent, the dispersing agent, coupling agent, and the polymer(s).

Example 3

The printing process of dark color substrate with the plastisol composition of the present invention is illustrated in FIG. 1. The printing machine has 16 heads and 18 plates and is capable of printing 6 or 7 colors. The plates are positioned around the center of the printing machine and labeled as 1, 2, 3, 4, 5, 6, 7, 8, 9, 10, 11, 12, 13, 14, 15, 16, 17, and 18.

The plates serves the following roles: the first plate was used to infeed T-shirt; the second plate was used to print white underlay; the third plate was used for flash cure unit (at a temperature of between about 150° C. to 205° C.); the forth plate was optionally used for the second color printing; the fifth plate was used for the third color printing; the six plate was used for the forth color printing; the seventh plate was used for flash unit (at a temperature of between about 150° C. to 205° C.); the eighth plate was optionally used for cooling measure of heated plate; the ninth plate was used for the fifth color printing; the tenth plate was used for the sixth color printing; the eleventh plate was used for the seventh color printing; the twelfth plate was used for final flash cure unit (at a temperature of between about 200° C. to 250° C. for about 4 seconds) for complete fusion; the thirteenth plate was not used, or used for outfeed; the fourteenth plate was not used; the fifteenth plate was not used; the sixteen plate was not used; the seventeens plate was not used; the eighteenth plate was used to outfeed printed T-Shirt.

After the above steps, no additional curing or fusion process was necessary. Two or three designs can be printed with one equipment same time and impression per hour can be increased up to 1500.

It should be noted that any one of plates 12, 13, 14, 15 16, 17 and 18 can be used for outfeed. For example, in the event Plate 12 is used for outfeed, one or more of Plate 13, 14, 15, and 16 can be used to print a second design, plate 17 can be used for flash unit for final cure, and plate 18 can be used for outfeed for the second design print.

With the process described herein, electrically powered and/or gas fired conveyor fusion system is no longer necessary. With the elimination of conveyor thermo-fusion system, the consumption of energy and emission of gas waste can drastically cut down. Further, expensive hot flash adhesive is no longer necessary.

It will be understood by those of skill in the art that numerous and various modifications can be made without departing from the spirit of the present invention. Therefore, it should be understood that the various embodiments of the present invention described herein are illustrative only and not intended to limit the scope of the present invention.

The invention claimed is:

1. A plastisol composition comprising:
   (a) a first copolymer of vinyl chloride and vinyl acetate and optionally a second copolymer of vinyl chloride and vinyl acetate, wherein the second copolymer has a mean particle size that is at least about 30% bigger than the mean particle size of the first copolymer, and the ratio by weight between the first copolymer and the second copolymer ranges from about 4:1 to about 25:1 and
   (b) a plasticizer mixture comprising dioctyl terephthalate, dibutyl terephthalate, 2,2,4-trimethyl-1,3 pentanediol diisobutyrate and benzyl butyl 1,2-cyclohexyldicarboxylate, wherein the ratio between the weight of the 2,2,4-trimethyl-1,3 pentanediol diisobutyrate and the total weight of the first and second copolymers ranges from about 1:200 to 1:10.

2. The plastisol composition of claim 1, wherein less than about 5% by weight of the first copolymer is derived from vinyl acetate.

3. The plastisol composition of claim 1, which comprises both the first copolymer and the second copolymer.

4. The plastisol composition of claim 1, wherein the mean particle size of the first copolymer is less than about 0.075 mm.

5. The plastisol composition of claim 1, wherein the mean particle size of the second copolymer is bigger than about 0.085 mm.

6. The plastisol composition of claim 1, wherein the ratio between the total weight of the plasticizers and the total weight of the first and the second copolymers range from about 5:10 to about 9:10.

7. The plastisol composition of claim 1, wherein the ratio between the weight of the dioctyl terephthalate and the total weight of the first and second copolymers ranges from about 1:10 to 1:3.

8. The plastisol composition of claim 1, wherein the ratio between the weight of the benzyl butyl 1,2-cyclohexyldicarboxylate and the total weight of the first and second copolymers ranges from about 1:10 to 1:6.

9. The plastisol composition of claim 1, wherein the ratio between the weight of the dibutyl terephthalate and the total weight of the first and second copolymers ranges from about 1:4 to 1:2.

10. The plastisol composition of claim 1, further comprising at least one ingredient selected from the group consisting of a wetting agent, a dispersing agent, a crosslinking agent, a filler, a blowing agent, a rheology modifier, a thixotropic agent, a lubricant, an anti-static agent, a heat stabilizer, a pigment, a flame retardant, a foaming agent, a viscosity reducer, a dilatancy reducer, and an UV absorber.

11. The plastisol composition of claim 10, wherein the wetting agent and/or dispersing agent is selected from the group consisting of an alkoxylate, a polar acidic ester, an anionic electrolyte, an acidic polyether, polydimethylsiloxane, a fluoro-substituted polyacrylate, and any combination thereof.

12. The plastisol composition of claim 10, wherein the crosslinking agent is selected from the group consisting of a peroxide, a tri-acrylate, and any combination thereof.

13. The plastisol composition of claim 10, wherein the filler is selected from the group consisting of calcium carbonate, alumina trihydrate, micro sphere, silica, nepheline syenite, and any combination thereof.

14. The plastisol composition of claim 10, wherein the blowing agent is selected from the group consisting of an expandable microsphere, a copolymer of acrylate, and a combination thereof.

15. The plastisol composition of claim 10, wherein the rheology modifier and/or a thixotropic agent is silica.

16. The plastisol composition of claim 10, wherein the lubricant is selected from the group consisting of paraffin wax, polytetrafluoroethlene, and a combination thereof.

17. The plastisol composition of claim 10, wherein the anti-static agent is selected from the group consisting of an alkoxy titanate, an ammonium salt, and a combination thereof.

18. The plastisol composition of claim 1, which is substantially free from phthalate plasticizer.

19. The plastisol composition of claim 1, which is configured for being printed on a textile substrate.

20. A method of printing or coating the plastisol composition of claim 1 on a substrate, comprising:
   (a) applying the plastisol composition to a substrate; and
   (b) exposing plastisol composition to a UV or heat source to cure the composition.

21. The method of claim 20, wherein the plastisol composition is exposed to the heat source at a temperature of lower than about 115° C.

22. The method of claim 20, wherein the plastisol composition is exposed to the heat source at a temperature ranging from about 80° C. to about 115° C.

23. The method of claim 20, wherein the plastisol composition is exposed to the heat source for less than about 10 seconds.

24. The method of claim 20, wherein the plastisol composition is exposed to the heat source for less than about 5 seconds.

25. The method of claim 20, wherein the substrate comprises a material selected from polyester, polyethylene, acrylic, polypropylene, natural or synthetic leather, polyamide, cotton, and any combination thereof.

26. The method of claim 20, wherein the substrate is a textile substrate and the plastisol composition is printed on the substrate.

27. The method of claim 20, wherein one or more additional plastisol compositions are printed on the substrate prior to step (b).

* * * * *